United States Patent
Ohda et al.

(10) Patent No.: US 6,309,864 B1
(45) Date of Patent: Oct. 30, 2001

(54) PROCESS FOR PRODUCING FOREIGN PROTEINS

(75) Inventors: Toyoo Ohda; Tomoshi Ohya; Shinobu Kuwae; Masao Ohyama; Kaoru Kobayashi; Yahiro Uemura, all of Hirakata (JP)

(73) Assignee: Yoshitomi Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 09/402,162

(22) PCT Filed: Apr. 3, 1998

(86) PCT No.: PCT/JP98/01552

§ 371 Date: Dec. 22, 1999

§ 102(e) Date: Dec. 22, 1999

(87) PCT Pub. No.: WO98/44146

PCT Pub. Date: Oct. 8, 1998

(30) Foreign Application Priority Data

Apr. 3, 1997 (JP) .................................................. 9-085064

(51) Int. Cl.⁷ .............................. C12P 21/06; C07K 14/00
(52) U.S. Cl. ........................ 435/71.1; 435/69.1; 530/363
(58) Field of Search ................................ 435/252.3, 248, 435/404, 71.1, 407, 253.6, 254.11, 254.2, 254.21, 254.23, 255.1, 255.2, 255.21; 530/363

(56) References Cited

U.S. PATENT DOCUMENTS

| 5,334,512 | * | 8/1994 | Kobayashi et al. | ................. | 435/69.6 |
| 5,378,612 | * | 1/1995 | Nakahsima et al. | ................. | 435/69.6 |

FOREIGN PATENT DOCUMENTS

| 0 157 275 A1 | 10/1985 | (EP) . |
| 0 504 823 A2 | 9/1992 | (EP) . |
| WO 89/01028 | 2/1989 | (WO) . |
| WO 96/02661A1 | 2/1996 | (WO) . |

* cited by examiner

Primary Examiner—Karen Cochrane Carlson
(74) Attorney, Agent, or Firm—Sughrue, Mion, Zinn, Macpeak & Seas, PLLC

(57) ABSTRACT

A production method of a heterologous protein, comprising culturing a heterologous protein-producing host prepared by gene manipulation in a medium containing a fatty acid or a salt thereof, and a surfactant and harvesting the heterologous protein from the culture. The production amount of the heterologous protein produced by a heterologous protein-producing host can be increased. Moreover, since decomposition of the heterologous protein by an enzyme derived from the host can be inhibited, enabling large scale production of a heterologous protein.

4 Claims, No Drawings

PROCESS FOR PRODUCING FOREIGN PROTEINS

TECHNICAL FIELD

The present invention relates to an improvement in the method for production of heterologous protein comprising culturing a host transformed by gene manipulation.

1. Background Art

While a broad range of proteins useful as pharmaceuticals, such as human serum albumin (hereinafter to be referred to as HSA), which is a major protein component of plasma, and the like are produced by fractionation of body fluid, this method is confronted with difficulty in securing the starting material, and the produced preparations have a strong possibility of contamination with virus and the like. The advent of the recombinant DNA technology in recent years has enabled production of such proteins by microorganisms and cells, which encourages study and development of large scale production of heterologous protein by genetic engineering. However, the yield is still low and a large scale production has not been attainable.

The method for increasing the production of heterologous protein includes a method comprising adding a fatty acid or a salt thereof to a medium to increase production of recombinant HSA (hereinafter to be referred to as rHSA) (JP-A-4-293495), a method comprising adding a high concentration surfactant having a polyalkylene glycol group (Japanese Patent Application under PCT laid-open under kohyo No. 3-500969) and the like.

In view of such technical background, the present invention aims at increasing the production amount of heterologous protein by particularly improving culture conditions.

2. Disclosure of the Invention

The present inventors have conducted intensive studies in an attempt to solve the above-mentioned problems, and found that the production amount of a heterologous protein can be increased by culturing a heterologous protein-producing host prepared by gene manipulation in a medium containing a fatty acid or a salt thereof, and a surfactant, which resulted in the completion of the present invention.

Accordingly, the present invention provides the following.

(1) A production method of a heterologous protein, comprising culturing a heterologous protein-producing host prepared by gene manipulation in a medium containing a fatty acid or a salt thereof, and a surfactant, and harvesting the heterologous protein from the culture.

(2) The production method of (1) above, wherein the fatty acid has 10 to 26 carbon atoms.

(3) The production method of (1) above, wherein the medium contains a fatty acid or a salt thereof at a concentration of 0.01–10W/V %.

(4) The production method of (1) above, wherein the surfactant is a non-ionic surfactant having a molecular weight of 100–100,000.

(5) The production method of (1) above, wherein the medium contains a surfactant at a concentration of not more than 0.5 g/L.

DETAILED DESCRIPTION OF THE INVENTION

In the present invention, by the heterologous protein is meant a foreign protein which is not inherently produced by a host cell but which has come to be produced by transformation.

The heterologous protein-producing hosts disclosed in known publications and one that will be developed from now, which are prepared by gene manipulation and used in the present invention, are subject to no particular limitation as long as they can be prepared by gene manipulation and are capable of producing a heterologous protein. Specific examples thereof include a cell (e.g., *Eschenchia coli*, yeasts, *Bacillus subtilis* and the like), an animal cell and the like, which are genetically manipulated to produce a heterologous protein. Particularly, in the present invention, the host is preferably a yeast, which may be the genus Saccharomyces or the genus Pichia. Auxotrophic strain and antibiotic sensitive strain of these hosts can be also used. Preferably, *Saccharomyces cerevisiae* AH22 strain which is a G418 sensitive strain (a, his 4, leu 2, can 1), *Pichia pastoris* GTS115 strain (his 4, NRRL deposit No. Y-15851) and the like can be used.

The heterologous protein produced by a heterologous protein-producing host is not particularly limited and preferably exemplified by HSA and the like.

These heterologous protein-producing hosts can be prepared by a known method or a method analogous thereto.

For example, an HSA-producing host (or an HSA-producing strain) can be prepared by a method using a known HSA gene (JP-A-58-56684, JP-A-58-90515, JP-A-58-150517), a method using a novel HSA gene (JP-A-62-29985, JP-A-1-98486), a method using a synthetic signal sequence (JP-A-1-240191), a method using a serum albumin signal sequence (JP-A-2-167095), a method comprising integration of a recombinant plasmid on a chromosome (JP-A-3-72889), a method comprising fusion of hosts (JP-A-3-53877), a method comprising mutation in a medium containing methanol, a method using a mutant AOX2 promoter (JP-A-6-90768, JP-A-4-299984), expression of HSA by *Bacillus subtilis* (JP-A-62-25133), expression of HSA by yeast (JP-A-60-41487, JP-A-63-39576, JP-A-63-74493), expression of HSA by *Pichia* yeast (JP-A-2-104290) and the like.

Of these, the method causing mutation in a medium containing methanol is performed as follows. A plasmid having a transcription unit to express HSA under the control of AOX1 promoter is introduced into the AOX1 gene region of a suitable host, preferably *Pichia* yeast, specifically *Pichia pastoris* GTS115 strain by a conventional method to give a transformant (see JP-A-2-104290). This transformant has a weak proliferation capability in a medium containing methanol. Thus, according to the method disclosed in JP-A-4-299984, this transformant is cultured in a medium containing methanol to cause mutation and only the strain capable of growth is recovered. In this case, the concentration of methanol is approximately 0.0001%–5%. The medium may be synthetic or natural. The culture conditions are 15° C.–40° C., about 1 hour–1000 hours.

As long as the medium to be used for culturing a transformed host contains a fatty acid or a salt thereof, and a surfactant, it is subject to no particular limitation with regard to other components, and a medium known in this field is usually used. Culturing of a transformed host in a medium containing a fatty acid or a salt thereof, and a surfactant enables increase in the production amount of a heterologous protein. In addition, the enzyme that the host itself secretes is expected to suppress decomposition of the heterologous protein.

Examples of fatty acid preferably include those having 10 to 26 carbon atoms.

Examples of the aforementioned fatty acid include saturated and unsaturated fatty acids such as myristic acid, palmitic acid, palmitoleic acid, oleic acid, t-vaccenic acid, linoleic acid, linolenic acid, linoleic acid, arachidonic acid and the like. The salts of these fatty acids are, for example, alkali metal salt such as sodium salt, potassium salt, calcium salt and the like, alkaline earth metal salts and organic amine salts, with preference given to a medium containing oleic acid or a salt thereof.

The content of fatty acid in the medium is about 0.01–10 W/V %, preferably about 0.2–5 W/V %.

The surfactant to be used in the present invention is a non-ionic surfactant preferably having a high molecular weight of from 100 to 100,000.

Examples of the aforementioned non-ionic surfactant include polyalkylene glycol (e.g., polypropylene glycol having an average molecular weight of 1000–10,000, preferably 2,000–6,000), polyoxy-alkylene copolymer (e.g., polyoxyethylene-polyoxypropylene copolymer having an average molecular weight of 100–100,000, preferably 1,000–30,000), hydrogenated castor oil polyoxyalkylene derivative [e.g., hydrogenated castor oil polyoxyethylene (20)-ether, hydrogenated castor oil polyoxyethylene-(40)-ether, hydrogenated castor oil polyoxyethylene-(100)-ether and the like], castor oil polyoxyalkylene derivative[e.g., castor oil polyoxyethylene(20)-ether, castor oil polyoxyethylene-(40)-ether, castor oil polyoxyethylene-(100)-ether and the like], polyoxyethylenesorbitan fatty acid ester (e.g., polyoxyethylenesorbitan monooleate, polyoxyethylenesorbitan monostearate, polyoxyethylenesorbitan monopalmitate, polyoxyethylenesorbitan monolaurate and the like), sorbitan fatty acid ester, alkylphenolpolyoxyethylene ether, polyoxyethylenesorbit fatty acid ester, polyoxyethylene hydrogenated castor oil, polyglycerine fatty acid ester and the like. In particular, it is preferable that the medium should contain polyalkylene glycol, polyoxyethylenepolyoxypropylene copolymer (trademark Pluronic and the like), or polyoxyethylenesorbitan fatty acid ester (trademark Tween and the like).

The content of the surfactant in a medium is preferably not more than 0.5 g/L.

The medium may be a synthetic medium or a natural medium, with preference given to a synthetic medium. It may be a solid medium or liquid medium, preferably a liquid medium. For example, a synthetic medium generally contains various saccharides as a carbon source, urea, ammonium salt, nitrate and the like as a nitrogen source, various vitamins, nucleotide and the like as trace nutrients and inorganic salts (e.g., Mg, Ca, Fe, Na, K, Mn, Co, Cu and the like). Examples of the medium include a YNB liquid medium [0.7% yeast nitrogen base (manufactured by Difco), 2% glucose] and the like. Examples of the natural medium include a YPD liquid medium [1% yeast extract (manufactured by Difco), 2% bactopeptone (manufactured by Difco), 2% glucose]. When a methanol utilizing host is used, a medium containing methanol can be used. In this case, the concentration of methanol is preferably about 0.01–5%.

The medium used in the present invention can be prepared easily by adding a fatty acid or a salt thereof, and a surfactant to a conventionally known medium.

Other conditions for culturing are similar to those used for a conventional method.

The culture temperature is, for example, 15° C.–40° C., generally 20° C.–37° C. When the host is a yeast, it is preferably 20° C.–30° C., and when the host is bacteria, it is preferably 30° C.–37° C. The culture time is generally about 1 hour–1000 hours.

The culturing is performed by batch culture or fed batch culture or continuous culture with standing still or shaking, stirring or aeration, preferably fed batch using a fermenter. For example, high concentration glucose is added in portions to fed batch culture, avoiding high concentration substrate inhibition relative to producing cells, whereby high concentration cells and products are obtained (JP-A-3-83595) and the like.

It is preferable that a pre-culture should be performed before this culturing. The medium for pre-culture may be, for example, YNB liquid medium or YPD liquid medium. The conditions of pre-culture are preferably culture time of 10 hours–100 hours, temperature of about 30° C for yeasts, and about 37° C for bacteria.

After the completion of the culturing, a heterologous protein is harvested by a known method of separation and purification from the culture. As used herein, the culture covers any substance capable of containing a heterologous protein, such as a culture medium, a heterologous protein-producing host and the like, and the like obtained by culturing the host, which is specifically a culture supernatant, a filtrate thereof, a bacterial cell, a cell and the like.

The present invention is explained in detail in the following by way of Example and Experimental Example, to which the present invention is not limited.

EXAMPLE 1

(1) Preparation of Bacterial Strain Used

Using a mutant AOX2 promoter [natural AOX2 promoter (YEAST, 5, 167– 177 (1988) or Mol. Cell Biol., 9, 1316–1323 (1989)) wherein $255^{th}$ nucleotide upstream of initiation codon was changed from T to C], a plasmid pMM042 for HSA expression was constructed and introduced into Pichia pastoris GTS115 strain to give a transformant UHG42–3 strain (JP-A-4-29984).

(2) Composition of Medium

For pre-culture, YPD medium (2% bactopeptone, 1% yeast extract, 2% glucose) was used. The composition of batch medium used for main culture is shown in Table 1, and the composition of feed medium is shown in Table 2. The composition of the solution of *2 in Table 1 and Table 2 is shown in Table 3. As shown in Table 1 and Table 2, the oleic acid content of the batch medium and feed medium used in this Example was set to 0.5 W/V %.

TABLE 1

Composition of batch medium

| Component | Amount (1/L) |
|---|---|
| Glycerol | 50.0 g |
| $H_3PO_4$ (85%) | 14.0 ml |
| $CaSO_4.2H_2O$ | 0.6 g |
| $K_2SO_4$ | 9.5 g |
| $MgSO_4.7H_2O$ | 7.8 g |
| KOH | 2.6 g |
| Biotin solution (*1) | 1.6 ml |
| YTM solution (*2) | 4.4 ml |
| Oleic acid | 5.0 g |

(*1) biotin 0.2 g/L,
(*2) see Table 3

TABLE 2

Composition of feed medium

| Component | Amount (1/L) |
|---|---|
| YTM solution (*2) | 2.0 ml |
| Oleic acid | 5.0 g |
| Methanol | 1000.0 ml |

(*2) see Table 3

TABLE 3

Composition of YTM solution

| Component | Amount (1/L) |
|---|---|
| $FeSO_4 \cdot 7H_2O$ | 65.0 g |
| $CuSO_4 \cdot 5H_2O$ | 6.0 g |
| $ZnSO_4 \cdot 7H_2O$ | 20.0 g |
| $MnSO_4 \cdot 4-5H_2O$ | 3.0 g |
| $H_2SO_4$ | 5.0 ml |

(3) Culture Method Using Fermenter

① Pre-culture

A bacterial cell suspension (1 ml, about $OD_{540} \approx$ about 10) was inoculated to YPD medium (50 ml) and subjected to shake culture at 30° C. for 24 hours.

② Main culture

The pre-culture (14 ml) was inoculated to batch medium (700 ml) and subjected to aeration stirring culture in a mini-jar fermenter. The culture temperature was 25° C., pH was 5.8. Adekanol LG-109 (manufactured by Asahi Denka Kogyo), which is a polyoxyalkylene surfactant, was added to the medium to a concentration of 0.4 g/L.

In batch culture, when the yeast proliferated to a sufficiently high density and glycerol in the medium was consumed, feed medium was added and cultured for 360 hours to allow production of HSA.

After the completion of the culturing, the culture was sampled and the amount of HSA production was measured by the method described in the following examples. As a result, the amount was 114% when the production without oleic acid addition was 100%.

EXAMPLE 2

In the same manner as in Example 1 except that the oleic acid concentration of the feed medium was set to 1 W/V %, culturing was preformed. The amount of HSA production was 125%.

EXAMPLE 3

In the same manner as in Example 1 except that the oleic acid concentration of the feed medium was set to 5 W/V %, culturing was performed. The amount of HSA production was 127%.

EXAMPLE 4

In the same manner as in Example 1 except that the surfactant in the feed medium was Pluronic L-61 (average molecular weight 2,000, ethylene oxide:propylene oxide= 10:90, manufactured by Asahi Denka Kogyo), which is a polyoxyethylene-polyoxypropylene copolymer, culturing was performed.

Reference Example

Quantitative Determination of HSA Concentration

A part of the recovered culture was centrifuged and the supernatant was filtered after it became clear, which was followed by quantitative determination by gel filtration analysis by HPLC.

According to the present invention, the amount of the heterologous protein produced by a heterologous protein-producing host can be increased and decomposition of the heterologous protein by an enzyme secreted by the host itself can be inhibited, whereby the amount of heterologous protein harvested can be increased. The present invention comprises culturing of a heterologous protein-producing host in a medium containing a fatty acid or a salt thereof, and a surfactant, and is an easy and simple method.

This application is based on a patent application no. 9-85064 filed in Japan, the content of which is hereby incorporated by reference.

What is claimed is:

1. A production method of human serum albumin, comprising culturing a human serum albumin-producing microbial host prepared by gene manipulation in a medium containing a fatty acid having 10 to 26 carbon atoms or a salt thereof, and a surfactant and harvesting the human serum albumin from the culture.

2. The production method of claim 1, wherein the medium contains a fatty acid or a salt thereof at a concentration of 0.01–10 W/V %.

3. The production method of claim 1, wherein the surfactant is a non-ionic surfactant having a molecular weight of 100–100,000.

4. The production method of claim 1, wherein the medium contains a surfactant at a concentration of not more than 0.5 g/L.

* * * * *